United States Patent [19]

Tanaka et al.

[11] Patent Number: 5,068,400

[45] Date of Patent: Nov. 26, 1991

[54] FLUORINE-CONTAINING MONO- OR POLY-ALKYLENE GLYCOL AND METHOD FOR PRODUCING SAME

[75] Inventors: Masahide Tanaka, Iwakuni; Tokinori Agou, Saeki; Masahiro Kuwahara, Kuga; Takeshi Sakashita, Iwakuni; Tomoaki Shimoda, Kuga; Masaru Sudou, Otake, all of Japan

[73] Assignee: Mitsui Petrochemical Industries, Ltd., Tokyo, Japan

[21] Appl. No.: 214,188

[22] Filed: Jun. 29, 1988

[30] Foreign Application Priority Data

Jun. 29, 1987 [JP] Japan .................................. 62-161495
Jul. 15, 1987 [JP] Japan .................................. 62-177419

[51] Int. Cl.$^5$ ............................................. C07C 69/52
[52] U.S. Cl. .................................................. 560/223
[58] Field of Search ................. 560/223, 224; 860/223

[56] References Cited

U.S. PATENT DOCUMENTS

| 2,826,564 | 3/1958 | Bovey et al. | 560/223 |
| 4,079,084 | 3/1978 | Houghton | 260/615 |
| 4,080,507 | 3/1978 | Gresham | 560/223 |

FOREIGN PATENT DOCUMENTS

| 0073020 | 3/1983 | European Pat. Off. . |
| 0121918 | 10/1984 | European Pat. Off. . |
| 0152065 | 8/1985 | European Pat. Off. . |
| 0224099 | 11/1986 | European Pat. Off. . |
| 0240601 | 10/1987 | European Pat. Off. . |
| 3021447 | 12/1980 | Fed. Rep. of Germany . |
| 50-101306 | 8/1975 | Japan . |
| 50-1101307 | 8/1975 | Japan . |
| 0052019 | 9/1975 | Japan . |
| 52-33502 | 8/1977 | Japan . |
| 57-51705 | 3/1982 | Japan . |
| 57-56453 | 4/1982 | Japan . |
| 8194839 | 12/1983 | Japan . |
| 61-11308 | 5/1986 | Japan . |
| 1126052 | 6/1986 | Japan . |
| 8201546 | 5/1982 | World Int. Prop. O. . |

OTHER PUBLICATIONS

Patent Abstracts of Japan, Kokai No. 61-111308 (May 29, 1986).
Patent Abstracts of Japan, Kokai No. 57-51705 (Mar. 26, 1982).

*Primary Examiner*—Paul J. Killos
*Attorney, Agent, or Firm*—Sherman and Shalloway

[57] ABSTRACT

The novel fluorine-containing mono- or poly-alkylene glycol of this invention is a mono- or poly-alkylene glycol of the formula (I):

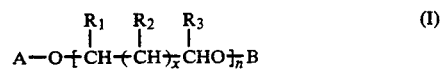

wherein $R^1$, $R^2$ and $R^3$ independently represent a hydrogen atom or an alkyl group having 1 to 30 carbon atoms, A represents a hydrogen atom, an unsaturated hydrocarbon group having 1 to 30 carbon atoms, a polar group or a polar group substituted with an unsaturated hydrocarbon group having 1 to 100 carbon atoms, B represents the same as the group selected from the group of A, provided that both A and B are not hydrogen atom, or a hydrocarbon group having 1 to 30 carbon atoms which may contain an oxygen atom or fluorine atom, x represents an integer of 0 to 100, and n represents an integer of 1 to 1000, the mono- or poly-oxyalkylene group in the main chain of the mono- or poly-alkylene glycol having at least one fluorine-substituted hydrocarbon group with 2 to 30 carbon atoms having at least 3 fluorine atoms bonded thereto graft-bonded onto the mono- or poly-oxyalkylene group in the main chain of the mono- or poly-alkylene glycol per one molecule of the mono- or poly-alkylene glycol.

1 Claim, 1 Drawing Sheet

FLUORINE-CONTAINING MONO- OR POLY-ALKYLENE GLYCOL AND METHOD FOR PRODUCING SAME

BACKGROUND OF THE INVENTION

1. Field of the Invention

The present invention relates to a novel fluorine-containing mono- or poly-alkylene glycol and a method for producing the same, more particularly it relates to a novel fluorine-containing mono- or poly-alkylene glycol to be used and the starting material in producing a polymer having an excellent oxygene permeability, water swellability and contamination resistance, and a method for producing the same.

2. Description of the Related Art

A polymer constituting a contact lens must have oxygen permeability, and as the material for such a lens, a polymer obtained by polymerization of a monomer such as methyl methacrylate or a methacrylic acid ester type compound has been used in the prior art. Nevertheless, most of these polymers have an inferior oxygen permeability and a lens made of such a polymer can not be worn for a long time.

To improve the oxygen permeability of a methacrylic acid ester polymer, it has been proposed to make contact lenses of a silicone methacrylate type polymer having siloxane bonds introduced into methacrylic acid ester molecules (see, for example, Japanese Patent Publication (Kokoku) No. 52-33502), of an oxygen permeable polymer composed mainly of cellulose acetate butyrate, and of a fluorine-containing methacrylate type polymer (see, for example, Japanese Unexamined Patent Publications (Kokai) Nos. 57-51705 and 61-111308). Although these polymers have an improved oxygen permeability, compared with the methacrylic acid ester type polymers such as polymethyl methacrylate of the prior art, they are still not satisfactory, and polymers having a further improved oxygen permeability are required. Also, these polymers do not have a satisfactory contamination resistance, hydrophilic property, and water swellability.

SUMMARY OF THE INVENTION

Accordingly, the objects of the present invention are to eliminate the above-mentioned problems of the prior art and to provide a novel fluorine-containing mono- or poly-alkylene glycol which can be used for preparing a polymer having an excellent oxygen permeability and an excellent hydrophilic property, water swellability, and contamination resistance, and to provide a method for producing the same.

Other objects and advantages of the present invention will be apparent from the following description.

In accordance with the present invention, there is provided a fluorine-containing mono- or poly-alkylene glycol derivative of the formula (I):

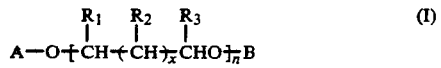

wherein $R^1$, $R^2$ and $R^3$ independently represent a hydrogen atom, or an alkyl group having 1 to 30 carbon atoms, A represents a hydrogen atom, an unsaturated hydrocarbon group having 1 to 30 carbon atoms, a polar group or a polar group substituted with an unsaturated hydrocarbon group having 1 to 100 carbon atoms, B represents the same as the group selected from the group of A, provided that both A and B are not hydrogen atom, or a hydrocarbon group having 1 to 30 carbon atoms which may contain oxygen atom or fluorine atom, x represents an integer of 0 to 100, and n represents an integer of 1 to 1000, the mono- or poly-oxyalkylene group in the main chain of the mono- or poly-alkylene glycol having at least one fluorine-substituted hydrocarbon group with 2 to 30 carbon atoms having at least 3 fluorine atoms bonded thereto graft-bonded onto the mono- or poly-oxyalkylene group in the main chain of the mono- or poly-alkylene glycol per one molecule of the mono- or poly-alkylene glycol.

In accordance with the present invention, there is also provided an method for producing a novel fluorine-containing mono- or poly-alkylene glycol comprising, obtaining a fluorine-containing mono- or poly-alkylene glycol of the formula (II) or (III):

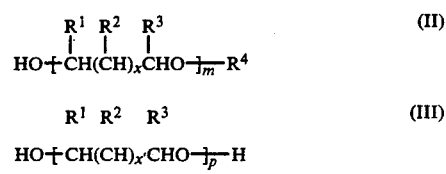

wherein each of $R^1$, $R^2$ and $R^3$ represents a hydrogen atom, an alkyl group having 1 to 30 carbon atoms, $R^4$ represents a hydrocarbon group having 1 to 30 carbon atoms which may also contain an oxygen atom or fluorine atom, x represents an integer of 0 to 100, x' represents an integer of 1 to 100, and m and p each represent an integer of 1 to 1000, the mono- or poly-oxyalkylene group in the main chain of the mono- or poly-alkylene glycol having at least one fluorine-substituted hydrocarbon group with 2 to 30 carbon atoms having at least 3 fluorine atoms bonded thereto graft-bonded onto the mono- or poly-oxyalkylene group in the main chain of the mono- or poly-alkylene glycol per one molecule of the mono- or poly-alkylene glycol, by allowing a mono- or poly-alkylene glycol represented by the above formula to react with a fluorine-substituted unsaturated hydrocarbon having 2 to 30 carbon atoms with at least 3 fluorine atoms bonded thereto.

In accordance with the present invention, there is further provided a method for producing the novel fluorine-containing mono- or poly-alkylene glycol derivative of the formula (IV):

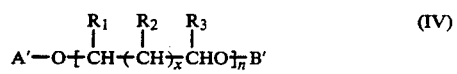

wherein $R^1$, $R^2$ and $R^3$ independently represent a hydrogen atom, an alkyl group having 1 to 30 carbon atoms, A' represents an unsaturated hydrocarbon group having 1 to 30 carbon atoms, a polar group or a polar group substituted with an unsaturated hydrocarbon group having 1 to 100 carbon atoms, B' represents the same as the group selected from the group of A' or a hydrocarbon group having 1 to 30 carbon atoms, x represents an integer of 0 to 100, and n represents an integer of 1 to 1000, the mono- or poly-oxyalkylene group in the main chain of the mono- or poly-alkylene glycol having at least one fluorine-substituted hydrocarbon group with 2 to 30 carbon atoms having at least 3 fluorine atoms bonded thereto, graft-bonded onto the mono- or polyoxyalkylene group in the main chain of the mono- or poly-alkylene glycol per one molecule of the mono- or poly-alkylene glycol, which comprises allowing a mono- or poly-alkylene glycol represented by the formula (III):

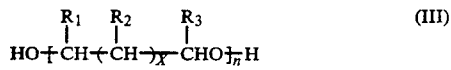

wherein $R_1$, $R_2$ and $R_3$ independently represent a hydrogen atom or an alkyl group having 1 to 30 carbon atoms, X represents an integer of 0 to 100 and n an integer of 1 to 1000 to react with a fluorine-substituted unsaturated hydrocarbon having 2 to 30 carbon atoms with at least 3 fluorine atoms bonded thereto to obtain a fluorine-containing mono- or poly-alkylene glycol having the fluorine-substituted hydrocarbon group derived from at least one fluorine-substituted unsaturated hydrocarbon graft-bonded onto the mono- or poly-oxyalkylene group in the main chain of the mono- or poly-alkylene glycol per one molecule of the mono- or poly-alkylene glycol, and subsequently allowing the fluorine-containing mono- or poly-alkylene glycol to react with one or two or more kinds of a polar group containing organic compounds.

BRIEF DESCRIPTION OF THE DRAWINGS

The present invention will be better understood from the description set forth below with reference to the accompanying drawing of FIG. 1, which shows an IR absorption chart of one example of the novel fluorine-containing polyalkylene glycol derivative according to the present invention.

DESCRIPTION OF THE PREFERRED EMBODIMENTS

Figure 1:
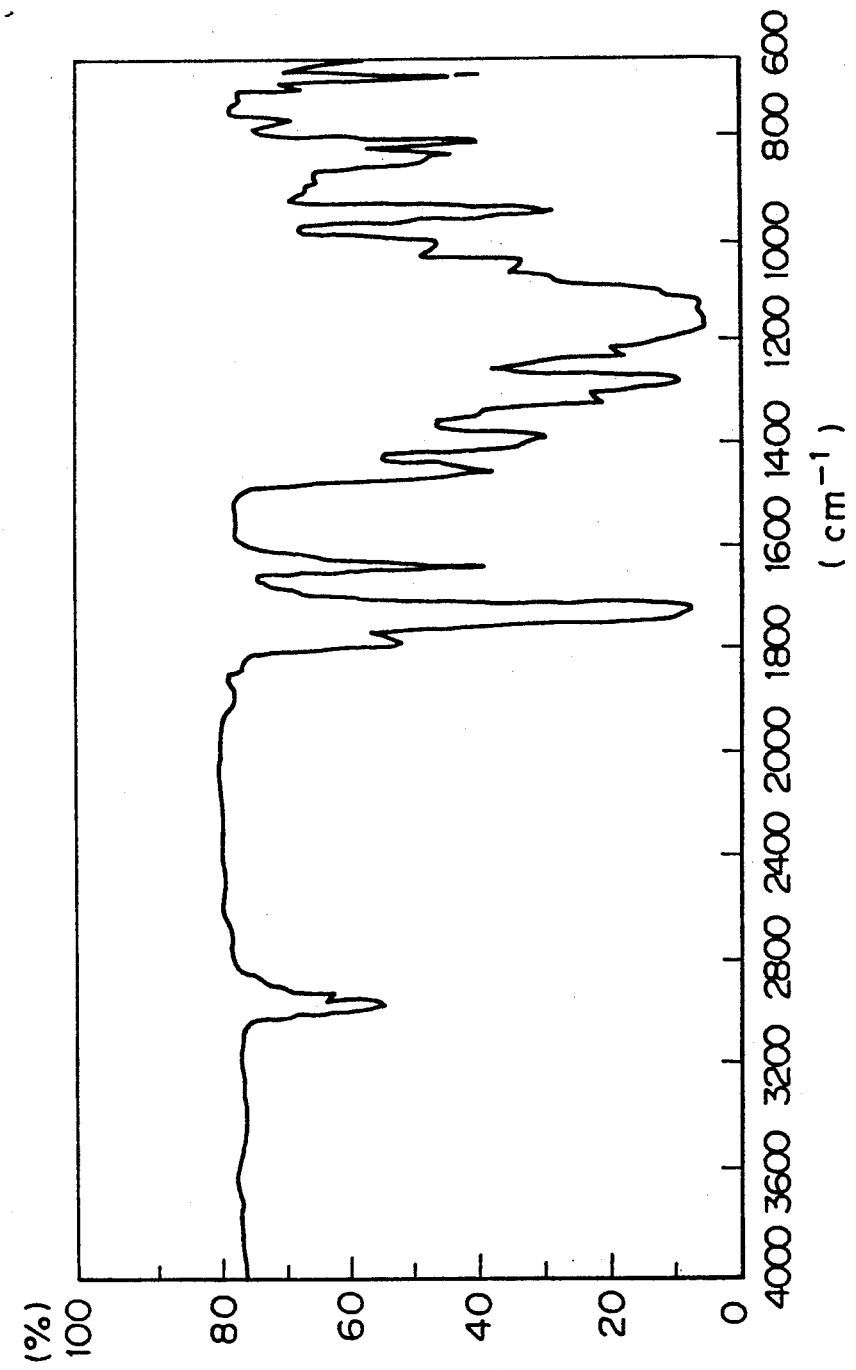

The novel fluorine-containing mono- or poly-alkylene glycol and the method for producing the same according to the present invention are now described in detail.

The novel fluorine-containing mono- or poly-alkylene glycol according to the present invention has at least one fluorine-substituted hydrocarbon group with 2 to 30 carbon atoms having at least 3 fluorine atoms bonded thereto grafted onto the mono- or poly-oxyalkylene group in the main chain of the mono- or poly-alkylene glycol represented by the above-mentioned formula (I) or the above-mentioned formulae (II), (III), and (IV).

In the above-mentioned general formulae, $R^1$, $R^2$ and $R^3$ each represent a hydrogen atom or an alkyl group having 1 to 30 carbon atoms, and specific examples of the alkyl group may include methyl, ethyl, propyl, isopropyl, butyl, isobutyl, sec-butyl, tert-butyl, pentyl groups.

A represents a hydrogen atom, an unsaturated hydrocarbon group, a polar group or a polar group substituted with an unsaturated hydrocarbon group having 1 to 100 carbon atoms.

Specific examples of such an unsaturated hydrocarbon group may include a vinyl group, allyl group, isopropenyl group, etc.

Specific examples of the polar group may include an aminocarbonyl group; $H_2N-CO-$, etc.

Further, the polar group substituted with an unsaturated hydrocarbon group may be exemplified by an acryloyl group ($CH_2=CHCO-$), methacrylolyl group ($CH_2=C(CH_3)CO-$), etc., preferably an acryloyl group or methacryloyl group.

B represents the same group as that selected from the group of A as described above or a hydrocarbon group having 1 to 30 carbon atoms which may contain an oxygen atom or fluorine atom. Specific examples of the hydrocarbon group may include alkyl groups such as methyl, ethyl, propyl, isopropyl butyl, isobutyl, sec-butyl, tert-butyl, and pentyl groups.

$R^4$ in the above formula (II) represents a hydrocarbon group having 1 to 30 carbon atoms, which preferably may also contain 0 to 61 oxygen atoms or fluorine atoms. More specifically, there may be included, $-CH_3$, $-C_2H_5$, $-C_4H_9$, $-C_6H_{12}$, $-C_{10}H_{21}$, $-C_{12}H_{25}$, $-C_{17}H_{35}$, $-C_{20}H_{41}$, $-CH(CH_3)_2$, $-C_6H_4C_9H_{19}$, $-COC_{17}H_{35}$, $CF_2CFH(CF_2)_6H$, $-COCF_3$, $-COC_2F_5$, $-COCH(CF_3)_2$, $-COC_7F_{15}$, $-COC_{10}F_{21}$, $-COCH_2CH_2C_7F_{15}$, $-COCH_2CF_3$ In the above-mentioned formulae, x is in the range of 0 to 100, preferably 0 to 30, and m, n and p are each in the range of 1 to 1000, preferably 1 to 500.

Specific examples of the mono- or poly-alkylene glycol represented by the above formula (I) according to the present invention may include the following compounds:

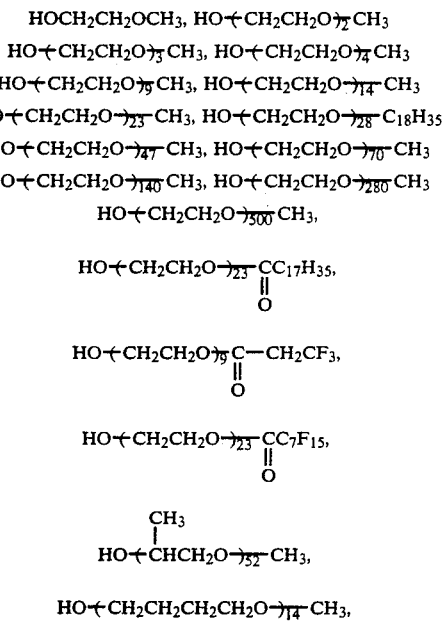

and mixtures thereof.

Other specific examples of the mono- and poly-alkylene glycol represented by the above formula (I) may include the following compounds:

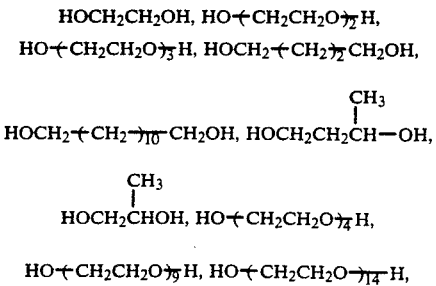

-continued

HO+CH₂CH₂O)₂₃H, HO+CH₂CH₂O)₄₇H,
HO+CH₂CH₂O)₇₀H, HO+CH₂CH₂O)₁₄₀H,
HO+CH₂CH₂O)₂₈₀H, HO+CH₂CH₂O)₅₀₀H, $$HO+CH_2\underset{\underset{CH_3}{|}}{CH}-O)_{25}H, HO+CH_2\underset{\underset{CH_3}{|}}{CHO})_{52}H,$$

HO+CH₂(CH₂)₂CH₂O)₁₄H,
HO+CH₂(CH₂)₂CH₂O)₂₈H, and mixtures thereof.

Further specific examples of the mono- or poly-alkylene glycol derivative represented by the above formula (I) according to the present invention may include mono- or poly-alkylene glycol derivatives substituted at the terminal ends with unsaturated hydrocarbon groups, such as:

CH₂=CH—O—CH₂—CHO—CH=CH₂
CH₂=CH—O+CH₂—CH₂O)₃CH=CH₂

$$CH_2=CH-O+\underset{\underset{CH_3}{|}}{CH}-CH_2O)_{23}-CH=CH_2$$

CH₂=CH—CH₂—O+CH₂—CH₂O)₇₆CH₂—CH=CH₂ mono- or poly-alkylene glycol derivatives substituted at the terminal ends with polar groups, such as:

H₂N—COO+CH₂—CH₂O)OC—NH₂
H₂N—COO+CH₂—CH₂O)₇₅OCNH₂

(meth)acrylic acid ester type mono- or poly-alkylene glycol derivatives, such as:

$$CH_2=\underset{\underset{H}{|}}{C}CO_2+CH_2CH_2O)_3CH_3$$

$$CH_2=\underset{\underset{CH_3}{|}}{C}CO_2+CH_2CH_2O)_3CH_3$$

$$CH_2=\underset{\underset{H}{|}}{C}CO_2+CH_2CH_2O)_9CH_3$$

$$CH_2=\underset{\underset{CH_3}{|}}{C}CO_2+CH_2CH_2O)_9CH_3$$

$$CH_2=\underset{\underset{H}{|}}{C}CO_2+CH_2CH_2O)_{14}CH_3$$

$$CH_2=\underset{\underset{CH_3}{|}}{C}CO_2+CH_2CH_2O)_{14}CH_3$$

$$CH_2=\underset{\underset{H}{|}}{C}CO_2+CH_2CH_2O)_{23}CH_3$$

$$CH_2=\underset{\underset{CH_3}{|}}{C}CO_2+CH_2CH_2O)_{23}CH_3$$

$$CH_2=\underset{\underset{CH_3}{|}}{C}CO_2+CH_2CH_2O)_3\underset{\underset{O}{\|}}{C}C_7F_{15}$$

$$CH_2=\underset{\underset{CH_3}{|}}{C}CO_2+CH_2CH_2O)_{23}\underset{\underset{O}{\|}}{C}C_7F_{15}$$

$$CH_2=\underset{\underset{CH_3}{|}}{C}CO_2+\underset{\underset{CH_3}{|}}{C}HCH_2O)_9CH_3$$

$$CH_2=\underset{\underset{CH_3}{|}}{C}CO_2+\underset{\underset{CH_3}{|}}{C}HCH_2O)_{23}CH_3,$$

$$CH_2=\underset{\underset{H}{|}}{C}CO_2+CH_2CH_2O)_{23}CO-\underset{\underset{H}{|}}{C}=CH_2$$

$$CH_2=\underset{\underset{CH_3}{|}}{C}CO_2+CH_2CH_2O)_{23}CO-\underset{\underset{CH_3}{|}}{C}=CH_2$$

$$CH_2=\underset{\underset{H}{|}}{C}CO_2+CH_2CH_2O)_{75}CO\underset{\underset{H}{|}}{C}=CH_2$$

$$CH_2=\underset{\underset{CH_3}{|}}{C}CO_2+CH_2CH_2O)_{75}CO\underset{\underset{CH_3}{|}}{C}=CH_2$$

$$CH_2=\underset{\underset{H}{|}}{C}CO_2(CH_2CH_2O)_{170}CO\underset{\underset{H}{|}}{C}=CH_2$$

$$CH_2=\underset{\underset{CH_3}{|}}{C}CO_2+(CH_2CH_2O)_{170}CO\underset{\underset{CH_3}{|}}{C}=CH_2$$

$$CH_2=\underset{\underset{H}{|}}{C}CO_2+\underset{\underset{CH_3}{|}}{C}HCH_2O)_{50}CO\underset{\underset{H}{|}}{C}=CH_2$$

$$CH_2=\underset{\underset{CH_3}{|}}{C}CO_2+\underset{\underset{CH_3}{|}}{C}HCH_2O)_{50}CO\underset{\underset{CH_3}{|}}{C}=CH_2$$

Specific examples of the fluorine-substituted hydrocarbon group having 2 to 30 carbon atoms with at least 3 fluorine atoms bonded thereto to be graft bonded onto such a mon- or poly-alkylene glycol of the formula (I) as described above may include the compounds shown below:

—CF₂CFHCF₃, —CF₂CFHC₂F₅, —CF₂CFHC₄F₉,
—CF₂CFHC₆F₁₃, —CF₂CFHC₁₀F₂₁, —CF₂CFHCF₂H,
—CF₂CFH(CF₂)₂H, —CF₂CFH(CF₂)₄H,
—CF₂CFH(CF₂)₆H, —CF₂CFH(CF₂)₇H,
—CF₂CFH(CF₂)₈H, —CF₂CFH(CF₂)₉H,
—CF₂CFH(CF₂)₁₀H, —CH₂CH₂C₂F₃, —CH₂CH₂C₂F₅,
—CH₂CH₂(CF₂)₆H, —CF₂CFHCF₂C(CF₃)₃,
—CF₂CFHCF₂CH(C₂F₅)₂,

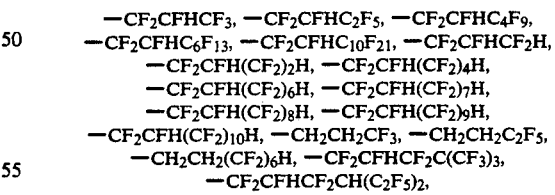

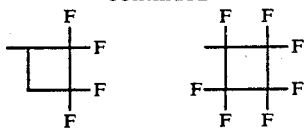

Preferably, the fluorine-substituted alkyl group has 2 to 20 carbon atoms with at least 3 fluorine atoms bonded thereto.

The fluorine-substituted hydrocarbon group is graft bonded to the alkylene group of the oxyalkylene group in the main chain of the mono- or poly-alkylene glycol represented by the above formula (I), and the grafting ratio of the fluorine-substituted hydrocarbon group is at least one, preferably 1 to 20 per one molecule of the mono- or poly-alkylene glycol, with the result that the fluorine-containing mono- or poly-alkylene glycol obtained has 3 to 400, preferably 3 to 200 fluorine atoms, per one molecules.

The fluorine-substituted hydrocarbon group having 2 to 30 carbon atoms with at least 3 fluorine atoms bonded thereto can be introduced into the compound represented by the formula (I) by allowing a fluorine-substituted unsaturated hydrocarbon having 2 to 30 carbon atoms with at least 3 fluorine atoms bonded thereto to react with a mono- or poly-alkylene glycol.

Examples of the fluorine-substituted unsaturated hydrocarbon as described above include the following compounds:

$CF_2=CFCH_3$, $CF_2=CFC_2H_5$, $CF_2=CFC_4F_9$,
$CF_2=CFC_6F_{13}$, $CF_2=CFC_{10}F_{21}$, $CF_2=CFCF_3$,
$CF_2=CFCF_2H$, $CF_2=CF(CF_2)_2H$, $CF_2=CF(CF_2)_4H$,
$CF_2=CF(CF_2)_6H$, $CF_2=CF(CF_2)_7H$, $CF_2=CF(CF_2)_8H$,
$CF_2=CF(CF_2)_9H$, $CF_2=CF(CF_2)_{10}H$, $CH_2=CHCF_3$,
$CH_2=CHC_2F_5$, $CH_2=CH(CF_2)_6H$, $CF_2=CFCF_2C(CF_3)_3$,
$CF_2=CFCF_2CH(C_2F_5)_2$, $CF_2=CF.CF=CF_2$,

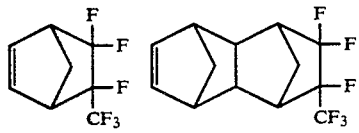

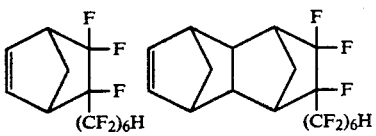

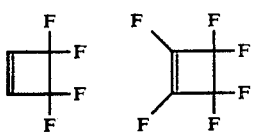

The novel fluorine-containing mono- or poly-alkylene glycol according to the present invention is a compound having at least one fluorine-substituted hydrocarbon group having 2 to 30 carbon atoms with at least 3 fluorine atoms bonded thereto as described above graft-bonded onto the mono- or poly-oxyalkylene group in the main chain of the mono- or poly-alkylene glycol per one molecule of the mono- or poly-alkylene glycol derivative, and specific examples thereof include the following (meth)acrylic acid ester type fluorine-containing mono- or poly-alkylene glycol derivatives:

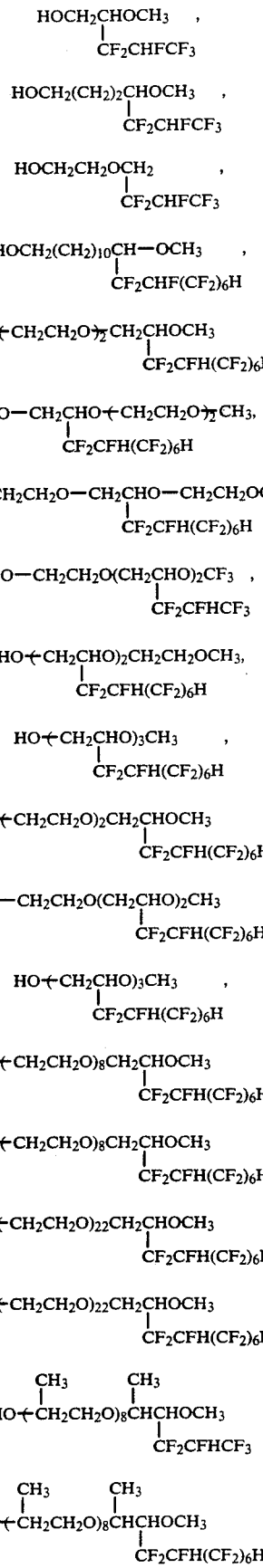

-continued
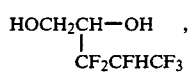
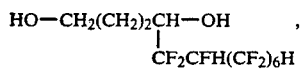
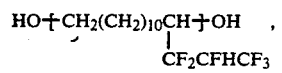
Here, p and q are integers and p+q is 1 to 1000.
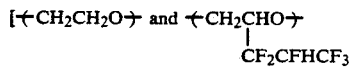
show random sequences, hereinafter the same.
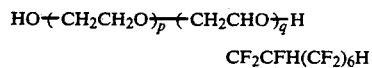
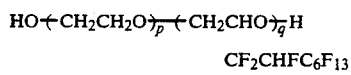
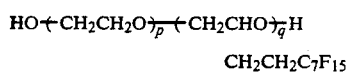
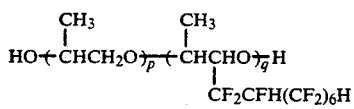
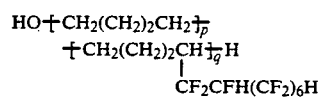
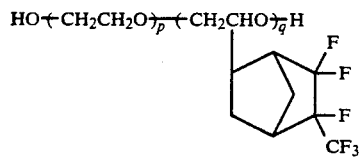
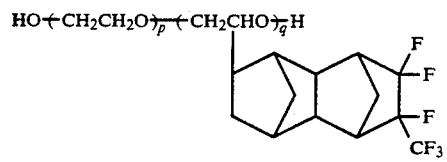
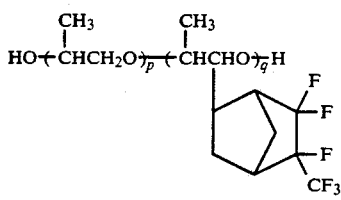
-continued
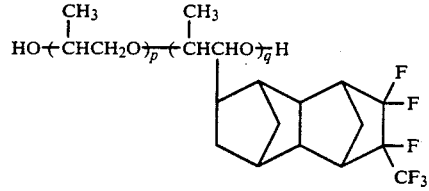
Further examples are as follows:
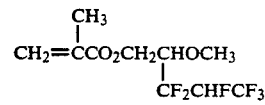
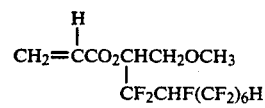
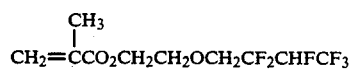
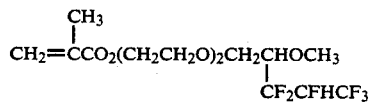
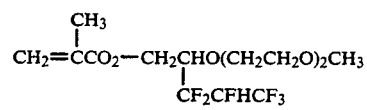
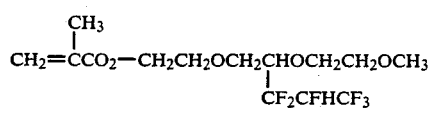
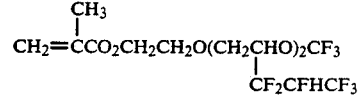
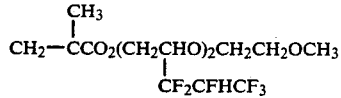
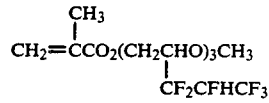
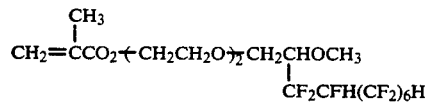
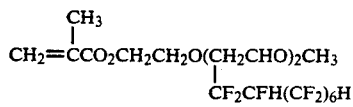
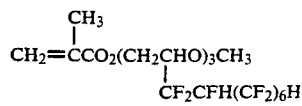

-continued $$CH_2=\overset{CH_3}{\underset{|}{C}}CO_2(CH_2CH_2O)_8CH_2\underset{|}{\overset{}{C}}HOCH_3$$
$$CF_2CFHCF_3$$

$$CH_2=\overset{CH_3}{\underset{|}{C}}CO_2(CH_2CH_2O)_8CH_2\underset{|}{\overset{}{C}}HOCH_3$$
$$CF_2CFH(CF_2)_6H$$

$$CH_2=\overset{CH_3}{\underset{|}{C}}CO_2(CH_2CH_2O)_{22}CH_2\underset{|}{\overset{}{C}}HOCH_3$$
$$CF_2CFHCF_3$$

$$CH_2=\overset{CH_3}{\underset{|}{C}}CO_2(CH_2CH_2O)_{22}CH_2\underset{|}{\overset{}{C}}HOCH_3$$
$$CF_2CFH(CF_2)_6H$$

$$CH_2=\overset{CH_3}{\underset{|}{C}}CO_2(CH_2CH_2O)_8CH_2\overset{CH_3}{\underset{|}{C}}HOCH_3$$
$$CF_2CFHCF_3$$

(with additional CH_3 substituent on middle carbon)

$$CH_2=\overset{CH_3}{\underset{|}{C}}CO_2(CH_2CH_2O)_8CH_2\overset{CH_3}{\underset{|}{C}}HOCH_3$$
$$CF_2CFH(CF_2)_6H$$

$$CH_2=\overset{CH_3}{\underset{|}{C}}CO_2(\overset{CH_3}{\underset{|}{C}}HCH_2O)_8\underset{|}{\overset{}{C}}HCHOCH_3$$
$$CF_2CFH(CF_2)_6H$$

$$CH_2=\overset{CH_3}{\underset{|}{C}}COOCH_2\underset{|}{\overset{}{C}}HO\overset{CH_3}{\underset{|}{C}}OC=CH_2$$
$$CF_2CHF(CF_2)_5CF_3$$

$$CH_2=\overset{H}{\underset{|}{C}}COOCH_2\underset{|}{\overset{H}{C}}HO\overset{}{C}OC=CH_2$$
$$CF_2CHFCF_3$$

$$CH_2=\overset{CH_3}{\underset{|}{C}}COOCH_2\underset{|}{\overset{}{C}}HO\overset{CH_3}{\underset{|}{C}}OC=CH_2$$
$$CF_2CHF(CF_2)_6H$$

$$CH_2=\overset{CH_3}{\underset{|}{C}}COOCH_2\underset{|}{\overset{}{C}}HOCH_2CH_2O\overset{CH_3}{\underset{|}{C}}OC=CH_2$$
$$CF_2CHFCF_3$$

$$CH_2=\overset{H}{\underset{|}{C}}COOCH_2CH_2OCH_2\underset{|}{\overset{H}{C}}HO\overset{}{C}OC=CH_2$$
$$CF_2CHF(CF_2)_6H$$

$$CH_2=\overset{CH_3}{\underset{|}{C}}CO_2\!\!-\!\!(CH_2CH_2CH_2CH_2O)_m\!\!-$$

$$-(CHCH_2CH_2CH_2O)_n\overset{CH_3}{\underset{|}{C}}OC=CH_2$$
$$CF_2CHFCF_3$$

$$CH_2=\overset{CH_3}{\underset{|}{C}}CO_2\!-\!(CH_2CH_2O)_p\!-\!(CH_2CHO)_q\!OC\overset{CH_3}{\underset{|}{C}}=CH_2$$
$$CF_2CHFCF_3$$

$$CH_2=\overset{CH_3}{\underset{|}{C}}CO_2\!-\!(CH_2CH_2O)_p\!-\!(CH_2CHO)_q\!OC\overset{H}{\underset{|}{C}}=CH_2$$
$$CF_2CHF(CF_2)_6H$$

-continued $$CH_2=\overset{CH_3}{\underset{|}{C}}COO\!-\!C_4H_7\!-\!OCO\overset{CH_3}{\underset{|}{C}}=CH_2$$
$$CF_2CHFCF_3$$

$$CH_2=\overset{H}{\underset{|}{C}}COO\!-\!C_8H_{15}\!-\!OCO\overset{H}{\underset{|}{C}}=CH_2$$
$$CF_2CHFCF_3$$

$$CH_2=\overset{CH_3}{\underset{|}{C}}\!-\!COO\!-\!CH_2CHOCH_2CH_2O\!-\!CH_2CH_2OCOC=CH_2$$
$$CF_2CHFCF_3 \qquad\qquad CH_3$$

$$CH_2=\overset{CH_3}{\underset{|}{C}}CO_2\!-\!\!(CH_2CH_2O)_p\!\!-\!\!(CH_2CHO)_q\!COC\overset{CH_3}{\underset{|}{}}=CH_2$$

(with fluorinated polycyclic substituent: F, F, F, CF_3)

$$CH_2=\overset{CH_3}{\underset{|}{C}}CO_2\!-\!\!(\overset{CH_3}{\underset{|}{C}}HCH_2O)_p\!\!-\!\!(\overset{CH_3}{\underset{|}{C}}HCH_2O)_q\overset{CH_3}{\underset{|}{C}}OC=CH_2$$

(with fluorinated bicyclic substituent: F, F, F, CF_3)

$$CH_2=\overset{CH_3}{\underset{|}{C}}CO_2\!-\!\!(\overset{CH_3}{\underset{|}{C}}HCH_2O)_p\!\!-\!\!(\overset{CH_3}{\underset{|}{C}}HCHO)_q\overset{CH_3}{\underset{|}{C}}OC=CH_2$$

(with fluorinated polycyclic substituent: F, F, F, CF_3)

In the present invention, the fluorine-containing mono- or poly-alkylene glycol as described above can be produced according to the method as described below.

By allowing the mono- or poly-alkylene glycol as described above represented by the formulae (II) and (III):

$$HO\!-\!\!(CH(CH)_x\overset{R^1}{\underset{|}{C}}HO)_m\overset{R^2}{\underset{|}{}}\overset{R^3}{\underset{|}{}}R_4 \qquad (II)$$

$$HO\!-\!\!(CH(CH)_x\overset{R^1}{\underset{|}{C}}HO)_p\overset{R^2}{\underset{|}{}}\overset{R^3}{\underset{|}{}}H \qquad (III)$$

wherein $R^1$, $R^2$ and $R^3$ independently represent a hydrogen atom or an alkyl group having 1 to 30 carbon atoms, $R^4$ represents a hydrocarbon group having 1 to 30 carbon atoms which may also contain an oxygen atom or fluorine atom, x represents an integer of 0 to 100, and m and p each represent an integer of 1 to 1000, to react with the fluorine-substituted unsaturated hydrocarbon having 2 to 30 carbon atoms with at least 3 fluorine atoms bonded thereto as described above, a mono- or polyalkylene glycol having at least one fluorine-substituted hydrocarbon group with 2 to 30 carbon atoms having at least one fluorine-substituted hydrocarbon group derived from the fluorine-substituted unsaturated hydrocarbon graft-bonded onto the mono- or polyoxyalkylene group in the main chain of the mono- or poly-alkylene glycol per one molecule of the mono- or poly-alkylene glycol is obtained.

Furthermore, in the present invention, the fluorine-containing mono- or poly-alkylene glycol as described above can be produced according to the method as described below.

First, by allowing the mono- or poly-alkylene glycol as described above represented by the formulae (II):

(III)

wherein $R^1$, $R^2$ and $R^3$ independently represent a hydrogen atom or an alkyl group having 1 to 30 carbon atoms, $R^4$ represents a hydrocarbon group having 1 to 30 carbon atoms which may also contain oxygen atom or fluorine atom, x represents an integer of 0 to 100, and p represents an integer of 1 to 1000, to react with the fluorine-substituted unsaturated hydrocarbon having 2 to 30 carbon atoms with at least 3 fluorine atoms bonded thereto as described above, a mono- or poly-alkylene glycol having at least one fluorine-substituted hydrocarbon group with 2 to 30 carbon atoms having at least one fluorine-substituted hydrocarbon group derived from the fluorine-substituted unsaturated hydrocarbon graft bonded onto the mono- or poly-oxyalkylene group in the main chain of the mono- or poly-alkylene glycol per one molecule of the mono- or poly-alkylene glycol is prepared.

The reactions of the above mono- or poly-alkylene glycol with the above fluorine-substituted unsaturated hydrocarbon are carried out generally in the presence of a reaction initiator and a solvent. The reaction initiator to be used in carrying out the reaction specifically includes isobutyryl peroxide, 1-hexyl-peroxyneohexanoate, 2,4-dichlorobenzoylperoxide, octanoylperoxide, cumylperoxyoctoate, m-toluoylperoxide, benzoylperoxide, t-butylperoxyacetate, t-butylperoxybenzoate, t-butylcumylperoxide, di-tertiary-butylperoxide, t-butyl hydroperoxide, etc., and may be used in an amount of 0.1 mmol/liter to 10 mol/liter, preferably 10 mmol/liter, to 1 mol/liter.

Specific examples of the solvent to be used in the reaction include benzene, toluene, xylene, chlorobenzene, dichlorobenzene, benzotrifluoride, chlorobenzotrifluoride, xylene hexafluoride, etc.

The reaction may be carried out at 20° to 300° C., preferably 50° to 200° C., for 2 to 50 hours.

After completion of the reaction, the fluorine-containing mono- or poly-alkylene glycol is separated according to the following treatment. Namely, if the product is a liquid fluorine-containing mono- or polyalkylene glycol having a low molecular weight, the product can be distilled, or extracted by a solvent mixture of water and diethyl ether into diethyl ether, followed by concentration and distillation, to separate the fluorine-containing mono- or poly-alkylene glycol formed. If the product is a solid having a high molecular weight, separation can be effected only by concentrating the reaction product to evaporate the solvent and unreacted fluoroolefin.

Consequently, in the present invention, the fluorine-containing mono- or poly-alkylene glycol is allowed to react with one or two or more kinds of polar group containing organic compounds to obtain a fluorine-containing mono- or polyalkylene glycol derivative as described above having terminal hydroxyl groups of the fluorine-containing mono- or poly-alkylene glycol substituted with other groups as described above. Specific examples of the polar group containing organic compounds to be used during this reaction include:

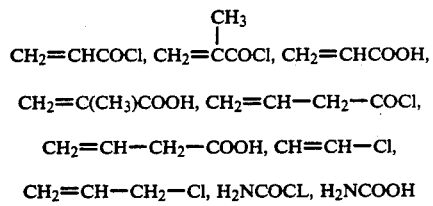

EXAMPLES

The present invention will now be further illustrated by, but is by no means limited to, the following Examples.

Example 1-1

A 100 ml stainless steel autoclave was charged with 20 g of ethylene glycol, 0.5 g of di-tert-butyl peroxide and 10 ml of benzotrifluoride as a solvent, tightly sealed, and then 10 g of hexafluoropropylene was charged into the reactor under pressure and the reaction was carried out under a pressure of 50 kg/cm$^2$ of nitrogen, while stirring at 140° C. for 5 hours.

After completion of the reaction, the mixture was cooled and gas purged therefrom, and the reaction mixture then withdrawn from the reactor. The reaction mixture was concentrated under a reduced pressure and the solvent evaporated. Extraction with diethyl ether and water washing was repeatedly conducted, and the ether layer was separated, followed by concentration, to isolate a crude product with a purity of 94% (according to gas chromatography). The product obtained was then distilled under a reduced pressure to obtain 8.5 g of 1,2-dihydroxy-3,3,4,5,5,5-hexafluoropentane with a purity of 98% (according to gas chromatography) (yield based on hexafluoropropylene: 60.1 mol %).

The compound obtained had the following physical properties and analytical results.

Boiling point: 58°–60° C./3–4 mmHg

|  | Elemental analytical values: | | |
| --- | --- | --- | --- |
|  | C (%) | H (%) | F (%) |
| Calculated | 28.30 | 2.83 | 53.77 |
| Found | 27.8 | 2.5 | 52.9 |

Gas chromatographic mass analysis:

According to the FI method the molecular ion peak mass was 213.

IR Absorptions observed at $\nu$OH 3350 cm$^{-1}$, $\nu$CF 1200 cm$^{-1}$.

$^1$H-NMR: (solvent for measurement: CD$_3$OD)
δ+3.80 (ethylene glycol portion —CH$_2$—)
δ=4.80 (ethylene glycol portion —CH—)
δ=5.24 Doublet-multiplet (—CF$\underline{H}$—$^2J_{HF}$=42 Hz, $^3J_{HF}$=7 Hz)

From the analytical results shown above, the product was confirmed to have the structure

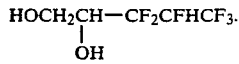

Examples 1-2 to 1-4

The same procedures as in Example 1-1 were conducted, except that the kind of alkylene glycol used in Example 1-1 was changed. The results are shown in Table 1-1.

Example 1-5

The reaction was conducted as in Example 1-1, except the kind of alkylene glycol, the kind of fluoroolefin, and the initiator in Example 1-1 were changed. The reaction product was concentrated under a reduced pressure and the reaction starting material was evaporated to isolate a reaction product. The results are shown in Table 1-1.

TABLE 1-1

| Ex-am-ple | Reaction material | | | Initiator g | Sol-vent ml | Reaction conditions | | Product |
|---|---|---|---|---|---|---|---|---|
| | Alkyleneglycol (g) | | Fluorine compound (g) | | | Temperature (°C.) | Time h | |
| 1-2 | Triethyleneglycol | 25.0 | $CF_2=CF.CF_3$ 15 | di-t-butyl peroxide 0.8 | — | 140 | 5 | $HOCH_2CHOCH_2CH_2OCH_2CH_2OH$ $CF_2CHFCF_3$ $HOCH_2CH_2OCHCH_2OCH_2CH_2OH$ $CF_2CHFCF_3$ $HOCHCH_2OCH_2CH_2OCH_2CH_2OH$ $CF_2CHFCF_3$ |
| 1-3 | Methylcellosolve | 13 | $CF_2=CF.CF_3$ 14 | di-t-butyl peroxide 0.8 | — | 140 | 5 | $HOCHCH_2OCH_3$, $HOCH_2CHOCH_3$ $CF_2CHFCF_3$ $CF_2CHFCF_3$ $HOCH_2CH_2OCH_2CF_2CHFCF_3$ |
| 1-4 | Triethyleneglycol monomethylether | 25 | $CF_2=CF.CF_3$ 15 | di-t-butyl peroxide 0.8 | — | 140 | 5 | $HOCH_2CHOCH_2CH_2OCH_2CH_2OCH_3$ $CF_2CHFCF_3$ $HOCH_2CH_2OCHCH_2OCH_2CH_2OCH_3$ $CF_2CHFCF_3$ $HOCH_2CH_2OCH_2CHOCH_2CH_2OCH_3$ $CF_2CHFCF_3$ $HOCH_2CH_2OCH_2CH_2OCHCH_2OCH_3$ $CF_2CHFCF_3$ |
| 1-5 | Methylcellosolve | 20 | $H(CF_2)_6CF=CF_2$ 5.0 | Benzoyl peroxide 0.3 | — | *3 100 | 6 | $HOCHCH_2OCH_3$, $CF_2CHF(CF_2)_6H$ $HOCH_2CHOCH_3$ $CF_2CHF(CF_2)_6H$ $HOCH_2CH_2OCH_2CF_2CHF(CF_2)_6H$ |

*3 normal pressure

| Example | Yield (yield %)*1 | Boiling point °C./mm Hg | Elemental Analysis C (%) H (%) F (%) | | | GC-MS analysis | | IR |
|---|---|---|---|---|---|---|---|---|
| 1-2 | 18.5 g (61.7%) | 110—110/1 | (Calculated 36.00, 4.67, 37.97) Found 36.4, 4.4, 38.2 | | | FI method Molecular ion mass | 301 | $\nu OH 3330\ cm^{-1}S$, $\nu$-$CH_2$ 2900 $cm^{-1}$ $\nu CF 1200\ cm^{-1}$, $\nu C$—O—C 1100 $cm^{-1}$ |
| 1-3 | 15.2 g (72.0%) | 43–69/26-10 | (Calculated 31.84, 3.54, 50.4) Found 30.6, 3.3, 51.2 | | | FI method Molecular ion mass | 227 | $\nu OH 3400\ cm^{-1}S$, $\nu$-$CH_2$ 2920 $cm^{-1}$, $\nu CH_3$ 2880 $cm^{-1}$, $\nu CF 1200\ cm^{-1}$, $\nu C$—O—C 1100 $cm^{-1}$ |
| 1-4 | 21.3 g (67.8%) | 89–98/1 | (Calculated 38.19, 5.09, 36.28) Found 37.3, 4.8, 38.1 | | | FI method Molecular ion mass | 315 | $\nu OH 3370\ cm^{-1}S$, $\nu$-$CH_2$ 2920 $cm^{-1}$, $\nu CH_3$ 2880 $cm^{-1}$, $\nu CF 1200\ cm^{-1}$, $\nu C$—O—C 1100 $cm^{-1}$ |
| 1-5 | 5.6 g (93.4%) | — | (Calculated 28.81, 1.96, 62.21) Found 29.8, 1.9, 61.0 | | | FI method Molecular ion mass | 459 | $\nu OH 3380\ cm^{-1}S$, $\nu$-$CH_2$ 2920 $cm^{-1}$, $\nu CH_3$ 2890 $cm^{-1}$, $\nu CF$ 1200 $cm^{-1}$, $\nu C$—O—C 1130 $cm^{-1}$ |

*1 based on fluoroolefin mol %

| Example | 1H NMR (solvent for measurement $CDCl_3$) |
|---|---|
| 1-2 | $\delta$ = 3.68–4.50 (Triethyleneglycol portion C$\underline{H}_2$C$\underline{H}$) $\delta$ = 5.20 Doublet multiplet (—CF$\underline{H}$ $^2J_{HF}$ = 42 Hz, $^3J_{HF}$ = 7 Hz) |
| 1-3 | $\delta$ = 3.38–3.40 (OC$\underline{H}_3$) $\delta$ = 5.0 Doublet multiplet (—CF$\underline{H}$ $^2J_{HF}$ = 42 Hz, $^3J_{HF}$ = 7 Hz) $\delta$ = 3.40–4.50 HOC$\underline{H}_2$C$\underline{H}_2$OC$\underline{H}_2$-Rf*4 $\underline{HOCHCH_2OCH_3}$ Rf*4 $\underline{HOCH_2CHOCH_3}$ Rf*4 |
| 1-4 | $\delta$ = 3.21 (OC$\underline{H}_3$) $\delta$ = 3.3–4.5 (Triethyleneglycolmonomethylether portion C$\underline{H}_2$, C$\underline{H}$, O$\underline{H}$) $\delta$ = 5.10 Doublet multiplet (—C$\underline{H}$F $^2J_{HF}$ = 42 Hz, $^3J_{HF}$ = 7 Hz) |
| 1-5 | $\delta$ = 3.40 (OC$\underline{H}_3$) |

TABLE 1-1-continued

δ = 3.4–5.9 (Methylcellosolve portion C$\underline{H}_2$, C$\underline{H}$, O$\underline{H}$)
δ = 6.0 triplet-triplet
($^2J_{HF} \approx$ 68 Hz, $^3J_{HF} \approx$ 5 Hz CF$_2\underline{H}$)
δ = 7.7 doublet multiplet
($^2J_{HF} \approx$ 50 Hz, $^3J_{HF} \approx$ 7 Hz CF$_2\underline{H}$

*4 —CF$_2$CHFCF$_3$

Example 1-6

A 300 ml eggplant type flask was charged with 40 g of polyethylene glycol (average molecular weight: 3,000), 7 ml (31.1 mol) of 8-H perfluorooctene-1, 1.0 g (4.1 mmol) of benzoyl peroxide, and 40 ml of chlorobenzene as a solvent, and the mixture was stirred at 100° C. for 5 hours under a nitrogen atmosphere. The solvent was removed from the reaction product by a rotary evaporator, the remaining product was dried at 100° C. with a vacuum pump, 300 ml of tetrahydrofuran was added thereto, and reprecipitation was effected with 3 liters of hexane with ice cooling under a nitrogen atmosphere. The precipitates obtained were filtered under a nitrogen atmosphere, followed by drying for several hours with a vacuum pump, to obtain 51.62 g of the desired polyethylene glycol derivative having fluoroalkyl group (yield: 98.5%).

IR 3425 cm$^{-1}$ νOH, 2900 cm$^{-1}$ ν—CH$_2$, 1470 cm$^{-1}$ νCH$_2$, 1210 cm$^{-1}$ νCF, 1120 cm$^{-1}$ νC—O—C $^1$H-NMR (solvent for measurement: CDCl$_3$)
δ=3.68 (ethylene glycol portion C$\underline{H}_2$)
δ=5.32 (—CF$\underline{H}$—)
δ=6.05 Triplet
(CF$_2\underline{H}$—$^2$J=50 Hz)

$^{13}$C-NMR (solvent for measurement: CDCl$_3$)
δ=61.4 (HO$\underline{C}$H$_2$CH$_2$O—)
δ=70.4 (—O$\underline{C}$H$_2$CH$_2$O—)
δ=72.3 (HO$\overline{CH_2C}$H$_2$O—)
δ=100–125 (—$\underline{C}$F$_n$—)$_n$=1 or 2

$^{19}$F-NMR (solvent for measurement)
δ=−210−−213 (C$\underline{F}_2$H)
δ=−136 (doublet)
J$_{FH}$=50 Hz (—C$\underline{F}$H—)
δ=−128 (CF$_2$H C$\underline{F}_2$—)
δ=−114−−122 (—C$\underline{F}_2$CFH(C$\underline{F}_2$)$_4$CF$_2$CF$_2$H)

GPC peak:
6.32×10$^3$
272×10$^4$
Mw/Mn=2.25

Ion chromatography
F content: 15.4% by weight

Glass transition temperature
Tm (°C.): 48.1
Crystallinity (%): 53.3

From the IR and NMR analytical results, it was determined that the structure is represented by the formula:

HO$+$CH$_2$CH$_2$O$)_{\overline{m}}+$CH$_2$CHO$)_{\overline{n}}$H
|
CF$_2$CFH(CF$_2$)$_6$H and from the average molecular weight and the F content, it was determined that the number of grafted fluoroalkyl groups is 1.6 and (CH$_2$CH$_2$O)$_m$ and

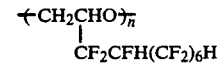

are arranged at random.

Since the values of Tm and crystallinity are lower than those of Comparative Example 1-1, it is understood that the obtained derivative is grafted.

Example 1-7

The same procedures as in Example 6 were conducted, except that 20 ml (88.9 mmol) of 8-H perfluorooctene-1 was used in Example 6 to obtain 69.3 g of a polyethylene glycol derivative having a fluoroalkyl group. The results are shown in Table 1-2.

Comparative Example 1-1

The same procedures as in Example 1-6 were conducted except that the 8-H perfluorooctene-1 used in Example 1-6 was omitted.

The results are shown in Table 1-2.

TABLE 1-2

| | Example 1-7 | Comparative Example 1-1 |
|---|---|---|
| Average molecular weight (GPC, in terms of polystyrene) | 5900 —CF$_2$CHF(CF$_2$)$_6$H | 5700 — |
| F content (% by weight) (ion chromatographic analysis) | 30.9 | 0 |
| Number of grafted groups | 3.3 | 0 |
| Tm °C. | 42.7 | 53.1 |
| Crystallinity | 32.5 | 73.5 |

Example 1-8

Into a 200 ml stainless steel autoclave 48 g of n-octane diol, 5.0 g of di-tert. butyl peroxide, and 70 ml of benzotrifluoride as a solvent were charged and, after sealing, 122 g hexafluoropropylene was charged under pressure, followed by allowing to react the mixture, while stirring, at 130° C. for 7 hours.

After completing the reaction, the reaction mixture was cooled and then the gas in the autoclave was purged, followed by withdrawing the reaction mixture therefrom. The reaction mixture was concentrated under a reduced pressure and the solvent was distilled off. The residue was extracted with diethyl ether, followed by repeatedly washing with water. The ether layer was separated. Thereafter, the residue was concentrated to isolate 48 g of the crude product. The crude product was further distilled under a reduced pressure to obtain 38 g of 1 or 2 or 3 or 4-hexafluoropropyl-1,8 octane diol isomers.

The physical properties and analytical data of the product are shown in Table 1-3.

Example 1-9

The same procedures as in Example 1-8 were conducted except that 150 g of n-pentane diol, 16 g of di-tert. butyl peroxide, 110 ml of a benzotrifluoride solvent, and 120 g of hexafluoropropylene were used. Thus, 152 g of 1 or 2 or 3-hexafluoro-1,5-pentanediol isomers were obtained.

The results are shown in Table 1-3.

Example 1-10

The same procedures as in Example 1-8 were conducted except that 14 g of n-butane diol, 0.8 g of di-tert. butyl peroxide, 10 ml of a benzotrifluoride solvent, and 16 g of hexafluoropropylene were used. Thus, 9.0 g of 1 or 2-hexafluoropropyl-1,4-butane diol was obtained.

The physical properties and analytical data of the product are shown in Table 1-3.

TABLE 1-3

| Example | Field *1 (%) | Boiling point (°C./mmHg) | Product | I.R. (neat. cm$^{-1}$) | Elemental analysis (%) Found (calculated) | $^{13}$C-NMR |
|---|---|---|---|---|---|---|
| 1-8 | 39.2 | 142–158/5 | HOCH(CH$_2$)$_{\overline{7}}$OH with CF$_2$CHFCF$_3$; HO—CH$_2$(CH$_2$)$_{\overline{6}}$OH with CF$_2$CHFCF$_3$; HO(CH$_2$)$_{\overline{2}}$CH(CH$_2$)$_{\overline{5}}$OH with CF$_2$CHFCF$_3$; HO(CH$_2$)$_{\overline{3}}$CH(CH$_2$)$_{\overline{4}}$OH with CF$_2$CHFCF$_3$ | νOH 3300–3400 νC—F 1200 | C 45.2 (44.6) H 5.6 (6.1) F 39.2 (38.5) | *2 |
| 1-9 | 41.3 | 122–139/3 | HOCH(CH$_2$)$_{\overline{4}}$OH with CF$_2$CHFCF$_3$; HOCH$_2$—CH(CH$_2$)$_{\overline{3}}$OH with CF$_2$CHFCF$_3$; HO(CH$_2$)$_{\overline{2}}$CH(CH$_2$)OH with CF$_2$CHFCF$_3$ | νOH 3300–3400 νC—F 1200 | C 36.2 (37.8) H 4.3 (4.7) F 46.1 (44.9) | *3 |
| 1-10 | 34.0 | 80–92/3 | HO—CH(CH$_2$)$_{\overline{3}}$OH with CF$_2$CHFCF$_3$; HO—CH$_2$CH(CH$_2$)$_{\overline{2}}$OH with CF$_2$CHFCF$_3$ | νOH 3300–3400 νC—F 1200 | C 34.6 (35.0) H 4.1 (4.2) F 49.0 (47.5) | — |

*1 based on the diol
*2 $^{13}$C NMR (Example 1-8)

| δ (ppm) | Moiety |
|---|---|
| 18–20 | HOC—C—<u>C</u>H$_2$— |
| 30.5, 31.3 | 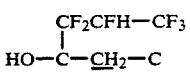 |
| 31.9, 32.1 | 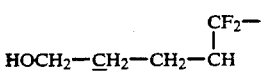 |
| 33–36 | 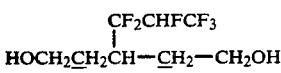 |
| 32.5, 33.8 | 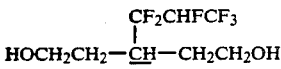 |
| 45.8, 46.4 | 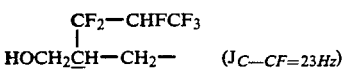 ($J_{C-CF}=23Hz$) |
| 57.5–59.1 | 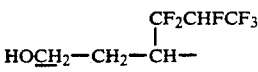 |
| 61.8, 64.3, 64.5 | 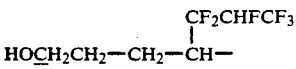 |

TABLE 1-3-continued

| | |
|---|---|
| 66.3, 68.5 | HOCH₂—CH—C— with CF₂CHFCF₃ substituent |
| 82.3–86.2 | HO—CH—C—C— with CF₂CHFCF₃ substituent ($J_{C-CF}=25Hz$) |
| 116.3, 116.9 | —C—C—C— with CF₂CHFCF₃ substituent ($J_{C-F}=153Hz$) |
| 120.0 | —C—CC—C— with CF₂—CHFCF₃ substituent ($J_{C-CF}=24Hz$) |
| | CF₂—CHFCF₃ ($J_{CF}=250Hz$, $J_{C-CF}=25.0Hz$) |

\*3 $^{13}$C NMR (Example 1-9)

| δ (ppm) | Moiety |
|---|---|
| 23.6 | HOCH₂CH₂CH₂— |
| 28.3 | HOCH₂CH₂CH₂CH₂ |
| 32.8 | HOCH₂CH₂CH₂— |
| 44–45 | HOCH₂—CH—CH₂— with CF₂—CHFCF₃ substituent ($J_{C-CF}=20.4Hz$) |
| 61.8 | HOCH₂CH₂— |
| 67.3–68.7 | HO—CH—CH₂— with CF₂—CHFCF₃ substituent ($J_{C-CF}=27.3Hz$) |
| 83.0–86.0 | HO—C—C—C— with CF₂—CFHCF₃ substituent ($J_{CF}=190.0Hz$, $J_{C-CF}=27.5Hz$) |
| 113–118 | COOC—C—C— with CF₂—CFHCF₃ substituent ($J_{C-F}=260Hz$, $J_{C-CF}=27Hz$) |
| 118–125 | COOC—C—C— with CF₂—CHFCF₃ substituent ($J_{C-CF}=28.0Hz$, $J_{C-CF}=26Hz$) |

Example 2-1

In a 100 ml flask were mixed, while stirring 6.0 g of 1,2-dihydroxy-3,3,4,5,5,5-hexafluoropentane, 10.3 g of methacrylic acid chloride, and 60 ml of tetrahydrofuran as a solvent, and 11.5 g of triethylamine was slowly added to the mixture dropwise under ice cooling over 1 hour. Subsequently, the mixture was allowed to react at 50° C. for 2 hours while stirring, methanol was added dropwise to the reaction mixture to decompose excessive methacrylic acid chloride, the reaction mixture was then filtered, and the filtrate was concentrated under a reduced pressure to obtain a crude product. Ethyl ether was added to the product obtained and the mixture was again filtered, and ether was evaporated from the filtrate under a reduced pressure, to obtain 9.3 g of the desired ethylene glycol dimethacrylate having fluoroalkyl group:

$$CH_2=\underset{CH_3}{\underset{|}{C}}-COOCH_2CHOCOC=CH_2$$
with CH₃ and CF₂CFHCF₃ substituents (GC purity: 98%).

| | Elemental analytical values | | |
|---|---|---|---|
| | C (%) | H (%) | F (%) |
| Calculated | 44.83 | 4.02 | 32.76 |
| Found | 45.1 | 4.3 | 31.9 |

Gas chromatographic analysis
  According to the FI method the molecular ion peak+1 mass was 349.
IR analysis chart is shown in FIG. 1.
  $\nu CO_2$ 1720 cm$^{-1}$, $\nu CH_2=C$- 1630 cm$^{-1}$, $\nu$C-F 1200 cm$^{-1}$ $^1$H-NMR analytical value (solvent for measurement: CDCl₃)

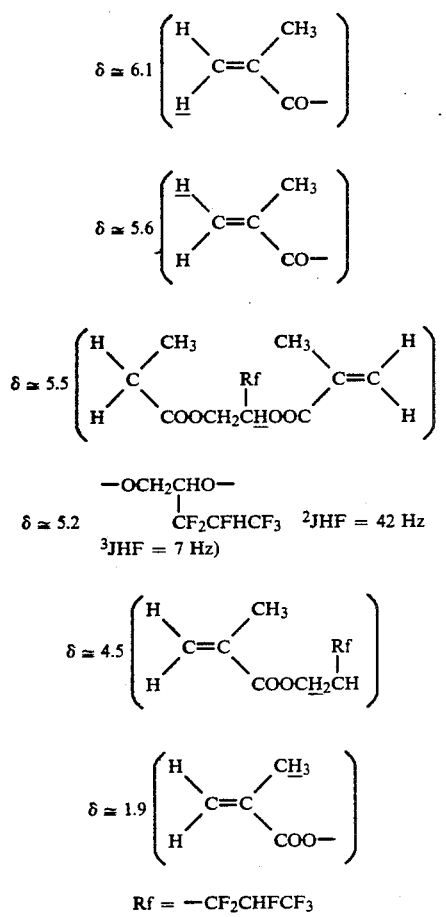

Example 2-2

The same procedures as in Example 2-1 were conducted except that an alkylene glycol grafted with fluoroalkyl group 7.1 g having a mixture of isomers of triethylene glycol in which one —CH$_2$CFHCF$_3$ group is grafted, $$\left\{\begin{array}{c}\text{CF}_2\text{CHFCF}_3\\|\\ \text{HOCH}_2\text{CHOCH}_2\text{CH}_2\text{OCH}_2\text{CH}_2\text{OH},\\ \text{CF}_2\text{CHFCF}_3\\|\\ \text{HOCH}_2\text{CH}_2\text{OCHCH}_2\text{OCH}_2\text{CH}_2\text{OH},\\ \text{CF}_2\text{CHFCF}_3\\|\\ \text{HOCHCH}_2\text{OCH}_2\text{CH}_2\text{OCH}_2\text{CH}_2\text{OH}\end{array}\right\}$$

6.6 g of methacrylic acid chloride and 7.4 g of triethylamine were used, to obtain 7.3 g of the desired triethylene glycol dimethacrylate having a fluoroalkyl group:

$$\text{CH}_2=\overset{\text{CH}_3}{\underset{|}{\text{C}}}\text{CO}_2\text{CH}_2\overset{\text{CF}_2\text{CFHCF}_3}{\underset{|}{\text{CH}}}\text{OCH}_2\text{CH}_2\text{OCH}_2\text{CH}_2\text{O}_2\overset{\text{CH}_3}{\underset{|}{\text{CC}}}=\text{CH}_2$$

$$\text{CH}_2=\overset{\text{CH}_3}{\underset{|}{\text{C}}}\text{CO}_2\overset{\text{CF}_2\text{CHFCF}_3}{\underset{|}{\text{CHCH}_2}}\text{OCH}_2\text{CH}_2\text{OCH}_2\text{CH}_2\text{O}_2\overset{\text{CH}_3}{\underset{|}{\text{CC}}}=\text{CH}_2$$

$$\text{CH}_2=\overset{\text{CH}_3}{\underset{|}{\text{C}}}\text{CO}_2\text{CH}_2\text{CH}_2\text{O}\overset{\text{CF}_2\text{CFHCF}_3}{\underset{|}{\text{CHCH}_2}}\text{OCH}_2\text{CH}_2\text{O}_2\overset{\text{CH}_3}{\underset{|}{\text{CC}}}=\text{CH}_2$$

| | Elemental analytical value | | |
|---|---|---|---|
| | C (%) | H (%) | F (%) |
| Calculated | 46.79 | 5.05 | 26.15 |
| Found | 45.3 | 4.8 | 27.5 |

Gas chromatographic analysis

According to the FI method the molecular ion peak+1 mass was 437.

IR analytical value $\nu$CO$_2$ 2950 cm$^{-1}$, $\nu$CO$_2$ 1720 cm$^{-1}$, $\nu$C=C 1640 cm$^{-1}$, $\nu$CF 1160–1220 cm$^{-1}$, $\nu$C—O—C 1100 cm$^{-1}$ $^1$H-NMR analytical value (solvent for measurement: CDCl$_3$)

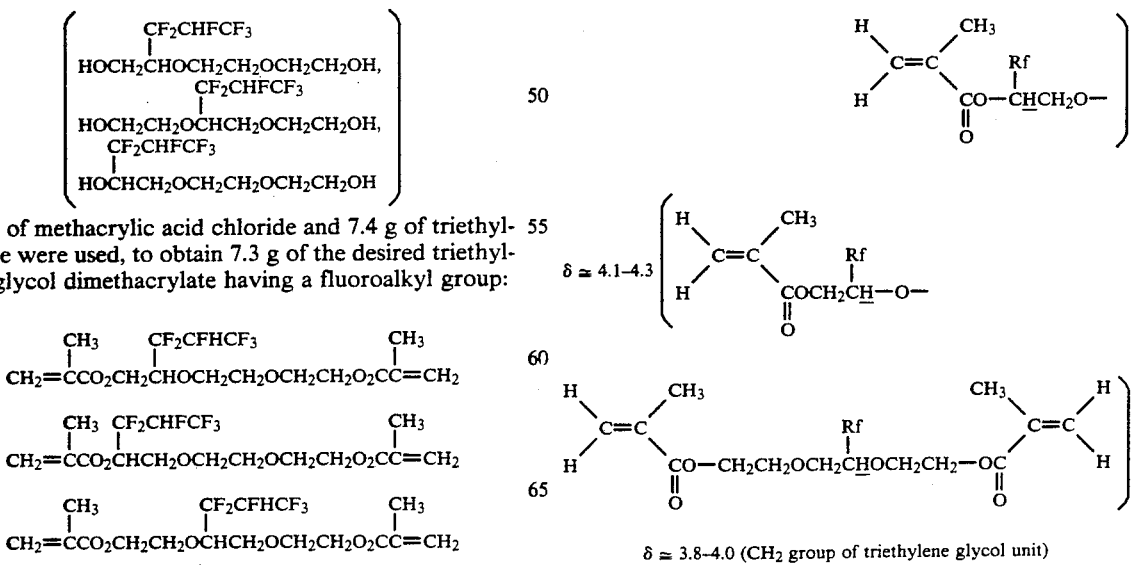

$\delta$ = 3.8–4.0 (CH$_2$ group of triethylene glycol unit)

-continued

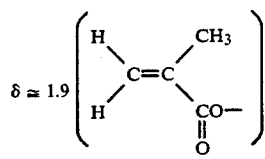

Rf = CF$_2$CFHCF$_3$

Example 2-3

The same procedures as in Example 2-1 were conducted except that an alkylene glycol containing fluoroalkyl group 9.7 g of mixture of methyl cellosolve having a

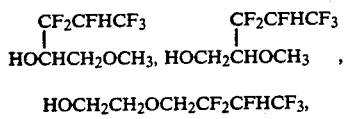

HOCH$_2$CH$_2$OCH$_2$CF$_2$CFHCF$_3$, 6.0 g of methacrylic acid chloride, and 6.4 g of triethylamine were used, to obtain 9.5 g of the desired monomethacrylate having fluoroalkyl group:

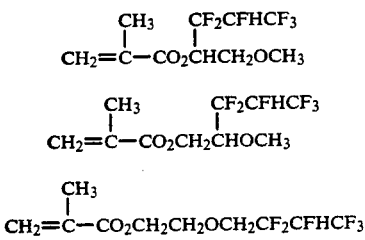

| | Elemental analytical values | | |
|---|---|---|---|
| | C (%) | H (%) | F (%) |
| Calculated | 40.82 | 4.08 | 38.78 |
| Found | 39.6 | 3.9 | 37.9 |

Gas chromatographic analysis
According to the FI method the molecular ion peak+1 mass was 295.
IR analytical value
$\nu$CH$_2$ 2920 cm$^{-1}$, $\nu$CH$_3$ 2880 cm$^{-1}$, $\nu$CO$_2$ 1720 cm$^{-1}$, $\nu$C=C' 1635 cm$^{-1}$, $\nu$CF 1160–1220 cm$^{-1}$, $\nu$C—O—C 1100 cm$^{-1}$
$^1$H-NMR analytical value (solvent for measurement: CDCL$_3$)

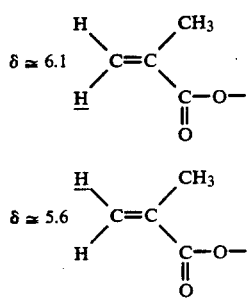

$\delta \simeq 5.3$ (—CF$_2$CFHCF$_3$ $^2$JHF = 42 Hz
$^3$JHF = 7 Hz)

-continued $\delta \simeq 4.5$–4.8

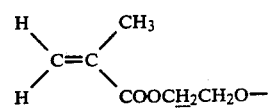

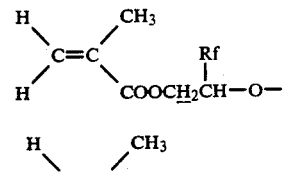

$\delta \simeq 3.6$–4.0

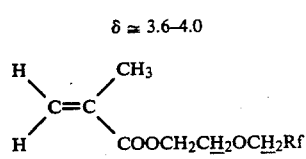

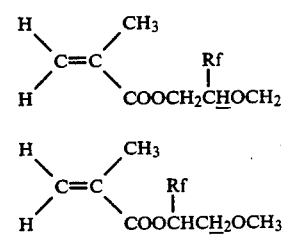

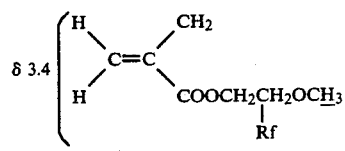

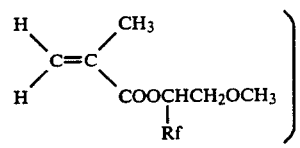

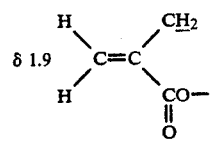

Rf = CF$_2$CFHCF$_3$

Example 2-4

A 1 liter four-necked flask was charged with 40 g of fluoroalkylated polyethylene glycol having —CF$_2$CHF(CF$_2$)$_6$H group (Mn: 6.2×10$^3$, F content: 15.4% by weight), 200 ml of trimethylamine, 200 ml of pyridine, and 200 ml of chloroform as a solvent, and 10 ml of methacrylic acid chloride was slowly added dropwise to the mixture under a nitrogen atmosphere. After completion of the dropwise addition, the temperature was elevated to 70° C. and the reaction was carried out for 1 hour. To the ice-cooled reaction mixture was added 100 ml of methanol, the mixture obtained was stirred at 40° C. for 1 hour to effect methylesterification of excessive methacrylic acid chloride, and thereafter, reprecipitation was carried out with 5 liters of ice-cooled hexane under a nitrogen atmosphere and the precipitates were filtered at a low temperature, 300 liters of THF were added thereto, and the mixture was filtered to remove insolubles. To the filtrate was added 1 g of p-methoxyphenol as a polymerization inhibitor, and the mixture was reprecipitated with 5 liters of hexane under ice cooling. The precipitates were filtered at a low temperature and then washed thoroughly with hexane, followed by drying for 3 hours with a vacuum pump, to obtain 32 g of the desired dimethacrylate derivative.

Ion chromatographic analysis:
F content: 12.8% by weight
G.P.C. analysis:
$Mn = 7.8 \times 10^3$
Tm (°C.): 50 (DSC analysis)
IR analytical values: $\nu$—$CH_2$ 2900 cm$^{-1}$, $\nu C\!=\!\!=\!C$ 1735 cm$^{-1}$, $\nu C\!=\!\!=\!C$ 1640 cm$^{-1}$, $\nu C$—F 1210 cm$^{-1}$, $\nu C$—O—C 1120 cm$^{-1}$ $^1$H-NMR analytical values (solvent for measurement: CDCl$_3$)

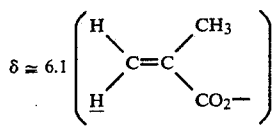

$\delta \simeq 6.0$ (—CF$_2$H $^2$JHF $\simeq$ 68 Hz $^3$JHF $\simeq$ 5 Hz)

$\delta \simeq 5.3$ (—CF$_2$CHF(CF$_2$)$_6$ $^2$JHF $\simeq$ 50 Hz $^3$JHF $\simeq$ 7 Hz)

$\delta \simeq 3.6$ (polyethylene glycol portion —CH$_2$—)

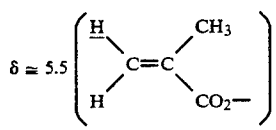

($^{13}$C-NMR analytical values (solvent for measurement CDCL$_3$)

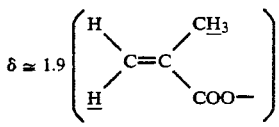

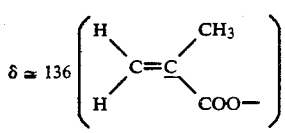

$\delta \simeq 105$–122 (—CF$_2$CFH(CF$_2$)$_6$H)

-continued
$\delta \simeq 82$ (—CF$_2$CFH(CF$_2$)$_6$H $^1$JCF $\simeq$ 190 Hz)

$\delta \simeq 70$ (—OCH$_2$CH$_2$O—)

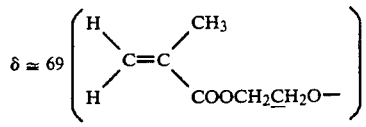

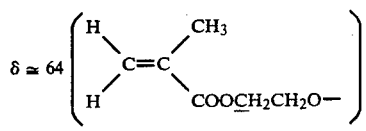

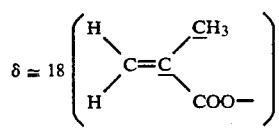

$^{19}$F-NMR analytical values (solvent for measurement: CDCL$_3$)
$\delta \simeq -210$ — $-213$ (CF$_2$H)
$\delta \simeq -136$ (—CFH—JFH$\simeq$50 Hz)
$\delta \simeq -128$ CF$_2$HCF$_2$—)
$\delta \simeq -144$ — $-122$ (—CF$_2$CHF(CF$_2$)$_4$CF$_2$H)

From the IR and NMR analytical results, it was determined that the structure is represented by the formula:

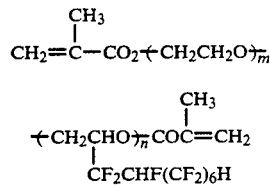

and based on the calculation of the average molecular weight and the F content, it was determined that the number of grafted fluoroalkyl groups is 2.0 and

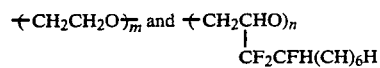

are arranged at random.

Since the Tm value is lower than that of Comparative Example 2-1, it is understood that the obtained derivative is grafted.

Example 2-5

The same procedures as in Example 4 were conducted except that fluoroalkylated polyethylene glycol having a —CF$_2$CHF(CF$_2$)$_6$H group (Mn: $5.9 \times 10^3$, F content: 30.9% by weight) was used to obtain 34 g of the desired dimethacrylate derivative.

According to the IR and NMR analytical results, the same absorption property as that of Example 2-4 was observed. The other results are shown in Table 2-1.

Example 2-6

A 1 liter four-necked flask was charged with 110 g of fluoroalkylated polyethylene glycol having —CF₂CHFCF₃ group (Mn: 7.7×10³, F content: 9.2% by weight), 30 g of methacrylic acid chloride, and 500 ml of tetrahydrofuran as a solvent, and 60 of triethylamine was slowly added dropwise to the mixture under a nitrogen atmosphere. The same procedures as in Example 2-4 were conducted thereafter to obtain 83 g of the desired dimethacrylate derivative.

The analytical values are shown in Table 2-1.

Example 2-7

The same procedures as in Example 2-4 were conducted except that a fluoroalkylated polyethylene glycol having a —CF₂CHFCF₃ group (Mn: 18.0×10³, F content: 18.8% by weight) was used to obtain 36 g of the desired dimethacrylate derivative.

The analytical values are shown in Table 2-1.

Comparative Example 2-1

The same procedures as in Example 2-4 were conducted except that polyethylene glycol (Mn: 6.5×10³) was used to obtain 34 g of the desired dimethacrylate derivative.

The analytical values are shown in Table 2-1.

TABLE 2-1

|  | Example 2-5 | Example 2-6 | Example 2-7 | Comparative Example 2-1 |
|---|---|---|---|---|
| Average molecular weight (GPC calculated on polystyrene) | 7076 | 7910 | 18700 | 6000 |
| Kind of grafted functionality | —CF₂CHF(CF₂)₆H | —CF₂CHFCF₃ | —CF₂CHFCF₃ | — |
| F content (wt. %) (Ion chromatographic analysis) | 27.7 | 7.9 | 18.5 | 0 |
| Tm °C. | 44.6 | 42.0 | 39.0 | 53.1 |

Example 2-8

A 100 ml four-necked flask was charged with 20.3 g of polypropylene glycol grafted with —CF₂CHFCF₃ group (Mn: 4.5×10³, F content: 8.5% by weight), 7.0 g of methacrylic acid chloride, and 50 ml of tetrahydrofuran as a solvent, followed by stirring under ice cooling, and 14 g of triethylamine was slowly added dropwise to the mixture. The temperature was then elevated to 60° C., and the reaction was carried out for 1 hour. To the reaction mixture, which had been again ice cooled, 7.0 ml of methanol was slowly added dropwise, and the mixture was allowed to react at 40° C. for 1 hour. The reaction mixture was filtered and the filtrate was concentrated, followed by vacuum drying, to obtain 18.3 g of the desired liquid dimethacrylate derivative.

The average molecular weight calculated on polystyrene according to GPC analysis was Mn: 4.4×10³, and the F content according to ion chromatographic analysis was 7.9% by weight. The IR analysis showed that the derivative had the absorption properties of $\nu$CH₂ 2900 cm⁻¹, $\nu$CH₃ 2850 cm⁻¹, $\nu$C=O 1720 cm⁻¹, $\nu$C=C 1640 cm⁻¹, $\nu$C—F 1180–1210 cm⁻¹, $\nu$C—O—C 1100 cm⁻¹.

According to ¹H NMR analysis (solvent for measurement: CDCl₃), the following signals were observed.

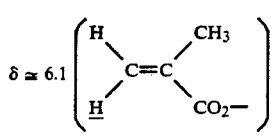

-continued

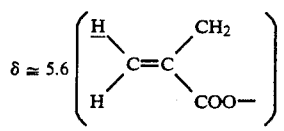

$\delta \cong 5.0$–5.4 (—CF₂CF<u>H</u>CF₃)

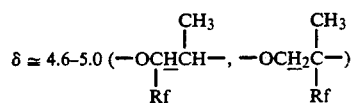

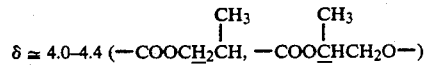

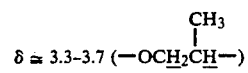

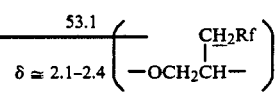

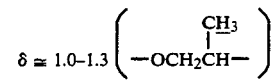

Rf = —CF₂CHFCF₃

From these results, it was formed that the product has the structure represented by:

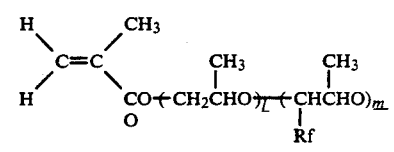

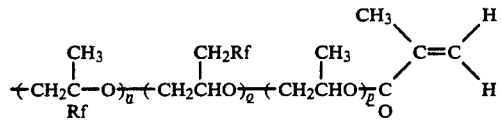

Rf: —CF₂CHFCF₃ in which the l, m, n, o and p groups are arranged at random.

Example 2-9

In a 500 ml flask were mixed, while stirring, 34 g of an isomer mixture of 1 or 2 or 3 or 4-hexafluoropropyl-1,8-octane diol, 36 g of methacrylic acid chloride, and 200 ml of a tetrahydrofuran solvent, and 55 g of htriethylamine was slowly added to the mixture dropwise under ice cooling over 2 hours. Subsequently, the mixture was allowed to react at room temperature for 2 hours while stirring. The methanol was added dropwise to the reaction mixture to decompose excessive methacrylic acid chloride, the reaction mixture was then filtered, and the filtrate was concentrated under a reduced pressure to obtain a curde product. Ethyl ether was added to the crude product obtained and the mixture was again filtered, and ether was distilled off from the filtrate under a reduced pressure, to obtain 37 g of the desired octane dimethacrylate having a hexafluoropropyl group.

The analytical results are shown in Table 2-2.

Example 2-10

The same procedures as in Example 2-9 were conducted except that 28.6 g of an isomer mixture of 1 or 2 or 3-hexafluoropropyl-1,5-pentane diol, 37.5 g of methacrylic acid chloride, 200 ml of tetrahydrofuran as a solvent, and 57.7 g of triethylamine were used. Thus, 27.6 g of the desired pentane dimethacrylate having a hexafluoropropyl group was obtained.

The results are shown in Table 2-2.

Example 2-11

The same procedures as in Example 2-9 were conducted except that 7.0 g of an isomer mixture of 1 or 2-hexafluoropropyl-1,4-butane diol, 6.5 g of methacrylic acid chloride, 100 ml of tetrahydrofuran as a solvent, and 9.7 g of triethylamine were used. Thus, 8.6 g of the desired butane dimethacrylate having a hexafluoropropyl group was obtained.

The results are shown in Table 2-2.

TABLE 2-2

| Example | Field (%) | Product | G.C. purity (%) | I.R. (neat. cm$^{-1}$) | Elemental analysis (%) Found (calculated) | $^{13}$C NMR |
|---|---|---|---|---|---|---|
| 2-9 | 74.6 | $CH_2=\overset{CH_3}{\underset{|}{C}}-CO_2-\overset{CF_2CHFCF_3}{\underset{|}{CH}}-(CH_2)_7-O_2C\overset{CH_3}{\underset{|}{C}}=CH_2$ <br> $CH_2=\overset{CH_3}{\underset{|}{C}}-CO_2-CH_2-\overset{CF_2CHFCF_3}{\underset{|}{CH}}\!\!-\!\!(CH_2)_6O_2C\overset{CH_3}{\underset{|}{C}}=CH_2$ <br> $CH_2=\overset{CH_3}{\underset{|}{C}}-CO_2\!\!-\!\!(CH_2)_2\overset{CF_2CHFCF_3}{\underset{|}{CH}}\!\!-\!\!(CH_2)_5O_2C\overset{CH_3}{\underset{|}{C}}=CH_2$ <br> $CH_2=\overset{CH_3}{\underset{|}{C}}-CO_2\!\!-\!\!(CH_2)_3\overset{CF_2CHFCF_3}{\underset{|}{CH}}\!\!-\!\!(CH_2)_4O_2C\overset{CH_3}{\underset{|}{C}}=CH_2$ | 98.6 | $\nu CO_2$ 1720 <br> $\nu CH_2=C$ 1630 <br> $\nu C-F$ 1200 | C 52.3 (52.8) <br> H 6.1 (6.0) <br> F 25.0 (26.4) | *1 |
| 2-10 | 62.9 | $CH_2=\overset{CH_3}{\underset{|}{C}}-CO_2-\overset{CF_2CHFCF_3}{\underset{|}{CH}}\!\!-\!\!(CH_2)_4O_2C\overset{CH_3}{\underset{|}{C}}=CH_2$ <br> $CH_2=\overset{CH_3}{\underset{|}{C}}-CO_2CH_2-\overset{CF_2CHFCF_3}{\underset{|}{CH}}\!\!-\!\!(CH_2)_3O_2C\overset{CH_3}{\underset{|}{C}}=CH_2$ <br> $CH_2=\overset{CH_3}{\underset{|}{C}}-CO_2\!\!-\!\!(CH_2)_2\overset{CF_2CHFCF_3}{\underset{|}{CH}}\!\!-\!\!(CH_2)_2O_2C\overset{CH_3}{\underset{|}{C}}=CH_2$ | 96.9 | $\nu CO_2$ 1720 <br> $\nu CH_2=C$ 1638 <br> $\nu C-F$ 1200 | C 49.0 (49.2) <br> H 5.3 (5.1) <br> F 29.6 (29.2) | *2 |
| 2-11 | 84.0 | $CH_2=\overset{CH_3}{\underset{|}{C}}-CO_2-\overset{CF_2CHFCF_3}{\underset{|}{CH}}\!\!-\!\!(CH_2)_3O_2C\overset{CH_3}{\underset{|}{C}}=CH_2$ <br> $CH_2=\overset{CH_3}{\underset{|}{C}}-CO_2CH_2-\overset{CF_2CHFCF_3}{\underset{|}{CH}}\!\!-\!\!(CH_2)_2O_2C\overset{CH_3}{\underset{|}{C}}=CH_2$ | 92.6 | $\nu CO_2$ 1720 <br> $\nu CH_2=C$ 1640 <br> $\nu C-F$ 1200 | C 47.7 (47.9) <br> H 4.9 (4.8) <br> F 30.7 (30.3) | — |

*1 $^{13}$C NMR (Solvent: CDCl$_3$, Standard: 77.0 (CDCl$_3$))

O CF$_2$—CHF—CF$_3$

| δ (ppm) | Moiety |
|---|---|
| 17.7 | 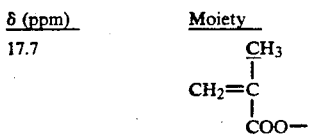 |
| 25.6 | 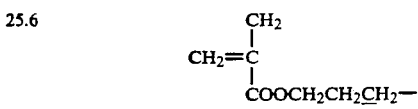 |

TABLE 2-2-continued

| δ | Moiety |
|---|---|
| 28.3 | CH₂=C(CH₃)—COOCH₂CH₂CH₂$\underline{CH_2}$— |
| 28.8 | CH₂=C(CH₃)—COOCH₂$\underline{CH_2}$CH₂— |
| 40–41. | CH₂=C(CH₃)—COO—CH₂$\underline{CH}$—CH₂— with CF₂—CHFCF₃ (JC—CF=20.3Hz) |
| 64.3 | C=C(CH₃)—COO$\underline{CH_2}$—CH₂— |
| 69.8–71.2 | C=C(CH₃)—COO—$\underline{CH}$—CH₂— with CF₂—CHF—CF₃ (JC—CF=27.1Hz) |
| 83–85.8 | COO—C—C—(C)— with CF₂$\underline{CHF}$—CF₃ (JCF=189.8Hz, JC—CF=27.0Hz) |
| 113–118 | COO—C—C—(C)—C— with $\underline{CF_2}$—CHF—CF₃ (JCF=255Hz, JC—CF=26Hz) |
| 118–125 | COO—C—C—(C)— with CF₂—CHF—$\underline{CF_3}$ (JC—F 278Hz, JC—CF 27Hz) |
| 124.5, 126.8, 129.9. | $\underline{CH_2}$=C(CH₃)—COO— |
| 134.0, 135.0, 136.2. | CH₂=C(CH₃)|—COO— |
| 163.5, 163.6, 165.2, 165.4, 167.0. | CH₂=C(CH₃)—$\underline{CO}$—O |

*2 ¹³C NMR (Solvent: CDCl₃, Standard: 77.0 (CDCl₃))

$$\underset{O}{\overset{CH_2-CHF-CF_2}{\parallel}}\quad O$$

| δ (ppm) | Moiety |
|---|---|
| 17.4–17.8 | C=C($\underline{CH_3}$)—COO— |
| 20, 21.2, 21.3, 22 | C=C(CH₃)—COOCH₂CH₂—$\underline{CH_2}$— |

TABLE 2-2-continued

| Shift | Structure |
|---|---|
| 26.5, 27.3 | C=C(CH₃)(CH₂CHF—CF₃) / COOC—CH₂CH₂— |
| 27.9, 28.1 | C=C(CH₃) / COO—CH₂—CH₂—CH₂CH—CH₂ with CF₂—CFH—CF₃ |
| 29.0–32 | C=C(CH₃) / COO—CH₂—CH₂—CH—CH₂— with CH₂—CFH—CF₃ |
| 34.5, 35.8 | C=C(CH₃) / COO—CH₂—CH₂—CH—CH₂— with CF₂—CFH—CF₃ |
| 41.8, 42.4 | CH₂=C(CH₃) / COO—CH₂—CH—CH₂—C with CF₂—CFH—CF₃ (JC—CF=23Hz) |
| 60–61.6 | CH₂=C(CH₃) / COO—CH₂—CH₂—CH— with CF₂—CFH—CF₃ |
| 63.8–64.4 | CH₂=C(CH₃) / COO—CH₂—C—C—C—C— with CF₂—CFH—CF₃ |
| 66.8, 67.0 | CH₂=C(CH₃) / COO—CH₂—CH—CH₂— / CF₂—CFH—CF₃ |
| 68.8, 71.0 | CH₂=C(CH₃) / COO—CH—C—C with CF₂—CFH—CF₃ (JC—CF=25.0Hz) |
| 82.3–86.2 | CH₂=C(CH₃) / COO C—C—(C)— with CF₂—CHF—CF₃ (JC—F=150.8Hz, JC—CF=24Hz) |
| 116.2, 116.8 | CH₂=C(CH₃) / COO—C—C—(C)— with CF₂—CFH—CF₃ (JC—F=251.0Hz, JC—CF=25.1Hz) |
| 120.5 | C=C(C) / COO—C—C—C— with CF₂—CFH—CF₃ (JC—F=276Hz) |
| 124.7, 126.8, 128.3 | CH₂=C(CH₃) / COO—C— |

TABLE 2-2-continued

| | |
|---|---|
| 135.3, 135.7, 136.4 | 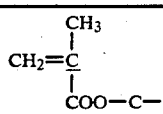 |
| 165.3, 165.6, 167.2 | 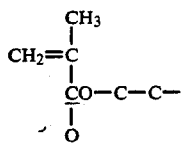 |

We claim:

1. A mono- or poly-oxyalkylene glycol acrylate of the formula (V)

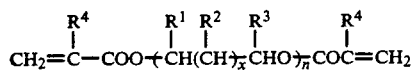

wherein $R^4$ represents hydrogen or methyl;

$R^1$, $R^2$ and $R^3$ independently represent hydrogen or an alkyl group having 1 to 30 carbon atoms;

x represents an integer of 0 to 100; and n represents an integer of 1 to 1000;

the mono- or poly-oxyalkylene group in the main chain of said mono- or poly-alkylene glycol having at least one fluorine-substituted hydrocarbon group with 2 to 30 carbon atoms having at least 3 fluorine atoms bonded thereto graft-bonded onto the mono- or poly-oxyalkylene group in the main chain of the mono- or poly-oxyalkylene group in the main chain of the mono- or poly-alkylene glycol per one molecule of the mono- or poly-alkylene glycol.

* * * * *